United States Patent [19]
Chen et al.

[11] Patent Number: 4,774,365
[45] Date of Patent: Sep. 27, 1988

[54] PERVAPORATION PROCESS FOR SEPARATING ALCOHOLS FROM ETHERS

[75] Inventors: Michael S. Chen, Zionsville; Robert M. Eng, Allentown; Jerome L. Glazer, Allentown, all of Pa.; Charles G. Wensley, Villa Park, Calif.

[73] Assignee: Air Products and Chemicals, Inc., Allentown, Pa.

[21] Appl. No.: 125,516

[22] Filed: Nov. 25, 1987

[51] Int. Cl.$^4$ .................. C07C 41/06; C07C 41/34
[52] U.S. Cl. .................. 568/697; 568/699; 585/324; 585/328; 585/639; 585/818
[58] Field of Search .......... 568/697, 699; 585/324, 585/328, 639, 818

[56] References Cited

U.S. PATENT DOCUMENTS

| | | | |
|---|---|---|---|
| 3,726,942 | 4/1973 | Louder | 260/683.61 |
| 3,846,088 | 11/1974 | Brown et al. | 44/56 |
| 4,118,425 | 10/1978 | Herbstman | 260/614 A |
| 4,218,569 | 8/1980 | Chase et al. | 568/697 |
| 4,302,298 | 11/1981 | Mikitenko et al. | 203/75 |
| 4,324,924 | 4/1982 | Torck et al. | 568/697 |
| 4,334,964 | 6/1982 | Prezeij et al. | 203/14 |
| 4,405,409 | 9/1983 | Tusel et al. | 202/200 |
| 4,409,421 | 10/1983 | Herwig et al. | 585/833 |
| 4,447,653 | 5/1984 | Vora | 568/697 |
| 4,465,870 | 8/1984 | Herskovits | 568/697 |
| 4,544,776 | 10/1985 | Osterburg et al. | 568/697 |
| 4,547,530 | 10/1985 | McCreedy et al. | 521/139 |
| 4,570,026 | 2/1986 | Keyworth et al. | 585/312 |
| 4,590,098 | 5/1986 | Kazuse et al. | 427/244 |
| 4,591,440 | 5/1986 | Higashimura et al. | 210/640 |
| 4,605,787 | 8/1986 | Chu et al. | 568/697 |

FOREIGN PATENT DOCUMENTS 205562  1/1987  European Pat. Off. .

*Primary Examiner*—Howard T. Mars
*Attorney, Agent, or Firm*—Mark L. Rodgers; William F. Marsh; James C. Simmons

[57] ABSTRACT

The present invention is an improved process for separating alcohols from ethers and/or hydrocarbon raffinate in an etherification process. The excess alcohol reactant, which forms azeotrope mixtures with the product ethers and $C_4$–$C_7$ raffinate, is removed by passing the liquid azeotrope mixture over a pervaporation membrane which effectively breaks the azeotrope and permeates the alcohol with high flux and high selectivity. In a typical etherification process, one or more pervaporation membrane units can be located ahead of the ether/raffinate distillation step, in conjunction with the distillation step with a liquid side draw, after the distillation step, or a combination of any of the above. The present invention also provides an improved process for separating alcohols from ethers and/or hydrocarbon raffinate in an ether decomposition process for the production of high purity iso-alkene products. In this embodiment, one or more pervaporation membranes are used to recover alcohols from the decomposition product stream.

23 Claims, 3 Drawing Sheets

PERVAPORATION PROCESS FOR SEPARATING ALCOHOLS FROM ETHERS

TECHNICAL FIELD OF THE INVENTION

The present invention relates to a process for separating alcohols from ethers using pervaporation membranes. It particularly relates to removing alcohol present in the ether product stream of an etherification process.

BACKGROUND OF THE INVENTION

It is well known that alkyl tert-alkyl ethers can be produced by reacting a primary alcohol with a tertiary olefin from 4 to 7 carbon atoms over a suitable catalyst. Two such ethers of great commercial value as motor fuel octane enhancers are methyl t-butyl ether (MTBE) and t-amyl methyl ether (TAME). These are made by reacting isobutylene and isopentenes respectively with methanol.

Such etherification reactions are exothermic and equilibrium-limited. They are generally carried out in the liquid phase in one or two fixed bed catalytic reactors in series, and heat is removed by circulating liquid through external heat exchangers. Catalysts are generally strongly acidic ion exchange resins such as 'Amberlyst 15,' commercially available from Rohm and Haas Co. Other suitable catalysts are a bifunctional catalyst which is a macroporous, strongly acidic cation exchanger with sulfonic groups and a trace of palladium or a selective zeolite catalyst such as ZSM-5 or ZSM-11.

These etherification catalysts are so selective for the tertiary olefins-methanol reactions that the diolefins present in the particular feedstock (such as butadiene and $C_3$–$C_4$ acetylenes), the carbonyl compounds, and other paraffins are not reacted in the reactions.

The tertiary olefin conversions are generally limited in the range of 90 to 96% in a single reactor system using excess methanol. To achieve higher conversions, a two-stage reactor system using between 2 to 20% excess methanol is generally practiced. Excess alcohol is also beneficial to suppress polymerization of olefins to dimers and trimers. However, the excess methanol in the MTBE or TAME processes must be removed for recycle to the reactors and for high purity ether products and $C_4$ to $C_7$ raffinates. Unfortunately, methanol forms azeotrope mixtures with these ethers and $C_4$ to $C_7$ raffinates. Separation by ordinary distillation is very difficult and, as a result, both energy- and capital-intensive.

Several techniques have been disclosed in the prior art to remove methanol form etherification products.

U.S. Pat. No. 3,726,942 discloses a MTBE process in which the MTBE effluent stream is first sent to a distillation column to separate MTBE (bottom product) from $C_4$ raffinate (overhead product). The crude MTBE product is water washed to remove methanol. The crude $C_4$ raffinate is also water washed to remove methanol; alternatively, mol sieve is used to remove methanol. The methanol-water is separated by distillation and recycled to the MTBE reactor.

U.S. Pat. No. 3,846,088 discloses a similar process in which the crude MTBE product from the distillation column bottom is subject to water wash and then mixed with a paraffin ($C_5$–$C_{10}$) to reject the residual water. U.S. Pat. No. 4,118,425 discloses a process in which crude MTBE/TAME from the reactor is first subject to water wash and then to distillation to produce $C_4$–$C_5$ raffinate overhead and pure MTBE/TAME product bottom.

U.S. Pat. No. 4,302,298 discloses a MTBE process in which the reactor effluent mixture is fed to a distillation column to produce a MTBE bottom product. The overhead vapor is condensed and water-washed to remove methanol before refluxing; then methanol-water is separated by distillation. Similarly, U.S. Pat. No. 4,324,924 discloses a MTBE process including a water wash step after the second reactor/distillation sequence.

U.S. Pat. No. 4,334,964 discloses a MTBE/TAME process using a water wash step to recover and recycle methanol from the reactor effluent. The methanol-water separation is done in a distillation column with a side draw to remove tertiary alcohol. U.S. Pat. No. 4,544,776 discloses a similar process as above.

U.S. Pat. No. 4,409,421 discloses a process for preparing a pure tertiary olefin, in which alkanol and tertiary alkyl ether are separated by distillation followed by adsorption using synthetic ion exchange resins. In U.S. Pat. No. 4,447,653 an adsorptive separation step is used to remove methanol from overhead raffinate stream of the distillation column (with water wash); regeneration is achieved by passing hot recycle isoparaffin-rich stream throughout the adsorbent. U.S. Pat. No. 4,465,870 discloses a similar process as above, and using the adsorbent of Type 5A or 13X molecular sieves for methanol and MTBE removal from $C_4$ raffinate.

U.S. Pat. No. 4,605,787 discloses a MTBE process which uses small pore zeolites (3A, 4A, 5A and chabozite) for methanol/MTBE separation from the crude MTBE bottom stream of the distillation column. In EP-205562 the methanol is recovered from the distillation overhead crude $C_4$ raffinate stream) using Na cation form of zeolite (pore size is about 4A); the bed is regenerated by passing a hot $C_4$–$C_5$ hydrocarbon feed stream before entering the reactor.

U.S. Pat. No. 4,218,569 teaches the use of a glycol to remove methanol.

U.S. Pat. No. 4,405,409 discloses a membrane method and apparatus for dehydrating mixtures of organic liquids and water. Example mixtures are ethanol/water, isopropanol/water, ethylacetate/water and pyridine/water. An example membrane material is modified cellulose acetate. U.S. Pat. No. 4,547,530 discloses a pervaporation membrane comprising a blend or alloy of poly-2-oxazolines and thermal plastic polymers for separating ethanol/hexane mixtures. U.S. Pat. No. 4,590,098 discloses a process for producing a composite membrane by cross-linking silicone resin with the dense layer of polyimide resin, useful for water/ethanol pervaporation separation. U.S. Pat. No. 4,591,440 claims a membrane for liquid separation, which comprises mainly poly (sub-stituted acetylene), especially for ethanol/water separation.

U.S. Pat. No. 4,570,026 discloses a process for producing high purity isobutene by MTBE decomposition by contacting a vapor MTBE-containing stream over a fixed bed of acid cation exchange resin and separating isobutene from methanol and unreacted MTBE by distillation columns.

BRIEF SUMMARY OF THE INVENTION

In one embodiment the present invention is an improved etherification process for ether production, especially methyl t-butyl ether (MTBE) and t-amyl methyl ether (TAME), by incorporating one or more pervaporation membrane steps in the purification section downstream of the etherification reactors to remove alcohol from the product stream.

In a typical etherification reaction, ethers are produced by reacting an olefin with an alcohol in a reactor over a suitable catalyst. The product stream from the reactor is an alcohol/ether/hydrocarbon raffinate stream in which the alcohol forms azeotrope mixtures with both the ether and hydrocarbon raffinate. The hydrocarbon raffinate is separated from the desired ether product by conventional distillation. The present invention is a method for removing alcohols form the product stream to yield a high purity ether product. In accordance with the invention, the liquid alcohol/ether/raffinate stream from the etherification reactor is passed over a pervaporation membrane capable of breaking the azeotropes and having a high flux and high selectivity for alcohols to produce a gaseous alcohol permeate stream and a liquid ether/raffinate reject stream. The gaseous alcohol permeate stream is recycled to the etherification reactor to be reacted with additional olefin feed, while the liquid ether/raffinate reject stream is passed to a distillation column to produce a raffinate stream and a high purity ether product stream.

In addition to, or instead of, placing the alcohol-selective pervaporation membrane upstream of the distillation unit, one or more such membranes may be used in conjunction with the distillation unit with a liquid side draw feed from the distillation unit to the membrane, or alternatively placed downstream of the distillation unit to remove alcohol from the ether product stream or overhead raffinate stream recovered from the distillation.

The present etherification process provides a low energy and low capital cost method for alcohol recovery from the alcohol/ether/raffinate mixture produced in a typical etherification process. Over 90% of excess alcohol can be recovered from the reactor system while eliminating water or glycol wash steps, or other complex prior art techniques such as adsorptive separation or entrainer and extractive type azeotropic distillation.

In another embodiment of the present invention, alcohols may be separated and recovered from the decomposition product stream produced in an ether dissociation process for making high purity alkenes. Ethers are decomposed in a reactor over a fixed bed of acid cation exchange resin to produce a decomposition product stream which is passed to a distillation column. Alcohols are separated from the product stream using one or more pervaporation membranes placed upstream from, or in conjunction with, the distillation column.

DETAILED DESCRIPTION OF THE INVENTION

In one embodiment, the present invention is an improved etherification process for separating alcohols from ethers and hydrocarbon raffinate by incorporating one or more pervaporation membrane steps in the purification section downstream of the synthesis reactor for forming ethers, to recover alcohols from the product stream. In a typical etherification process, excess alcohol is mixed with alkene feed to form the corresponding ether product. The resultant product stream from such a reaction contains ether product, excess alcohol, and some unreacted hydrocarbon raffinate. The hydrocarbon raffinate in most instances will predominantly be made up of $C_4$-$C_7$ alkanes or alkenes, although a wide range of other hydrocarbons, along with some non-hydrocarbon components, may also be present. The excess alcohol tends to form azeotropes with both the ether product and the excess hydrocarbon raffinate. The present invention provides an efficient scheme for breaking the ether/alcohol azeotrope, to recover a purified ether product and alcohol recycle stream, and also, in certain embodiments, allows for the separation of alcohol from the hydrocarbon raffinate to yield a purified raffinate stream and also a second alcohol stream, which can be recycled to the original reaction step to be mixed with alkene feed.

Figure 1:
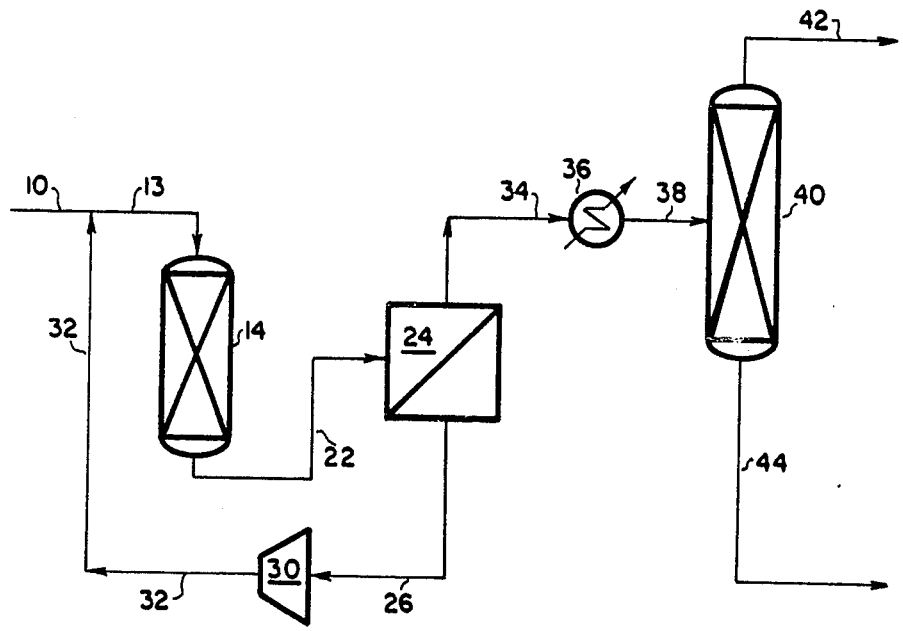
FIG. 1 is a schematic diagram of an etherification process according to the present invention wherein a pervaporation membrane is positioned upstream of the distillation unit.

A general description of one embodiment of the present invention for an etherification reaction can be had by reference to FIG. 1. A combined alcohol and alkene feed stream 10 is mixed with alcohol recycle stream 32, to form stream 13 which is passed to the etherification reactor 14, wherein the alcohol and alkene mixture is contacted with a suitable catalyst to form the corresponding ether. Generally any suitable alcohols and alkenes which are capable of reacting to form the corresponding ether can be used for this process. Commercially, however, the two most important reactions are the reaction of methanol with isobutene to form methyl t-butyl ether (MTBE) and the reaction of methanol with isopentenes to form t-amyl methyl ether (TAME). The ether product is then removed from the reactor 14 along with unreacted methanol, which is typically added in excess, and also hydrocarbon raffinate. This ether/alcohol/hydrocarbon raffinate stream 22 is passed to a pervaporation membrane 24 to separate the alcohol component from the ether and raffinate. The excess alcohol in stream 22 tends to form azeotropes with both the ether product and the raffinate present in the stream. Consequently, a membrane which is capable of breaking both the ether/alcohol azeotrope and also the raffinate/alcohol azeotrope should be used. Various membranes have been found to be suitable for this operation, examples being cellulose acetate (CA), polyvinyl alcohol (PVA), polysulfone, silicon rubber, and poly-substituted acetylenes, with the preferred membranes being CA and PVA. The membrane separation unit 24 may consist of one or more units which in turn may consist of a single membrane device or alternatively, several membrane devices plumbed and operated, so as to achieve the separation in the most efficient manner; e.g., a cascade of membranes with internal recycle streams between various stages of the membrane unit. Typically, the membrane devices are manufactured in modules, each having certain membrane areas for permeation and also appropriate interstage heat exchangers to compensate for the cooling effect due to pervaporation. The operating pressure of the membrane unit can range from about 1 atmosphere to 50 atmospheres, or higher, and the temperature from about 35° to 250° F. While generally the temperature and pressure are not critical, these conditions preferably are chosen such that the feed to the membrane, stream 22, is in the liquid state.

The membrane separation unit 24, separates the feed stream to form an alcohol-rich permeate vapor stream 26 and a ether/raffinate stream 34. The alcohol-rich permeate stream 26 typically comprising about 75% alcohol, is compressed and cooled in compressor/cooler system 30 to form compressed liquid alcohol stream 32, which is recycled and combined with the alcohol/alkene feed stream 10 to form stream 13 which is passed to the etherification reactor 14. The permeate side of the membrane separation unit 24 may be equipped with vacuum pumps, condensers, or a means of providing a sweep stream or carrier fluid in order to decrease the vapor pressure on the permeate side so as to achieve better permeation. All of these techniques are well known in the art, and can be employed as needed to achieve the most efficient operation of the particular membrane used.

The reject stream 34 from the membrane unit 24 contains predominantly ether product with excess hydrocarbon raffinate. The ether/raffinate stream 34 is heated in heat exchanger 36 to form stream 38 which is passed to a distillation unit 40. The ether/raffinate stream is treated in distillation column 40 to form an overhead raffinate stream 42 and a purified ether product stream 44. Typically, the purified ether product stream 44 has a concentration of at least 95% raffinate-free ether with little or no alcohol contaminants.

Figure 2:
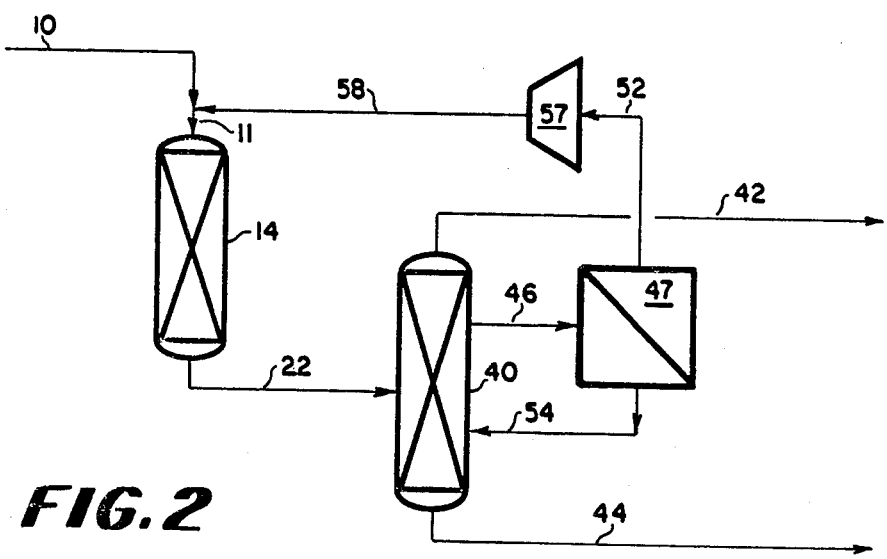
FIG. 2 is a schematic diagram of an etherification process according to the present invention wherein a pervaporation membrane is used in conjunction with the distillation unit, with a liquid side draw feed.

FIG. 2 shows an alternative embodiment of the present invention wherein the azeotropes are broken and alcohol is separated from the ether and raffinate by employing a pervaporation membrane which is fed with a side draw feed from the distillation column used to separate the ether from the raffinate. In accordance with this flow scheme an alcohol/alkene feed stream 10 is combined with alcohol recycle stream 58 to form feed stream 11 which is passed to an etherification reactor 14. The alcohol and alkenes are contacted with a suitable catalyst in the etherification reactor 14 to form an ether product, which together with excess alcohol and some hydrocarbon raffinate is recovered from the reactor as stream 22. This alcohol/ether/hydrocarbon raffinate stream 22 is passed directly to a distillation column 40 which is capable of separating the ether from the raffinate. A side draw feed 46 containing alcohol/ether/raffinate is withdrawn from the distillation column 40 and passed to a suitable membrane unit or units 47 to break the alcohol/ether and alcohol/raffinate azeotropes, and separate alcohol from the mixture. The alcohol is separated as permeate stream 52 in the vapor phase, and is condensed in compressor/cooler 57 to form a liquid alcohol stream 58 which is recycled and combined with the incoming alcohol/hydrocarbon feed 10 and fed as combined stream 11 to the etherification reactor 14. The reject stream 54 from the membrane separation unit 47 contains both ether and raffinate, and is returned to the distillation column 40 at a distillation tray below that from which the side draw feed was withdrawn. The combined ether/raffinate stream is further treated in the distillation column 40 to separate the raffinate as overhead stream 42 and recover ether product as purified ether stream 44 from the bottom of the distillation column 40. In accordance with this process nearly all of the alcohol present in the alcohol/ether/raffinate stream 22 from the etherification reactor 14 is recovered and recycled back to the feed 10. Additionally, the ether product is recovered having a $C_4$–$C_7$ raffinate-free ether concentration of 95%.

This invention solves the long standing problem of azeotrope mixture separation in MTBE or TAME processes. In conventional etherification processes, water wash to recover methanol is used to solve part of this problem, i.e., to break the $C_4$/methanol azeotrope at the expense of a significant capital and energy penalty. The other problem, i.e., the azeotrope mixture of MTBE/methanol is solved by a two-stage distillation with a significant amount of azeotrope mixture being recycled to the reactor system, and with a large amount of energy (steam) utilization. In contrast, the present invention is a simple process which utilizes pervaporation membrane systems to recover over 90% of excess methanol with high selectivity, thereby making $C_4$/MTBE distillation more efficient with much less energy consumed than with the prior art techniques.

Figure 4:
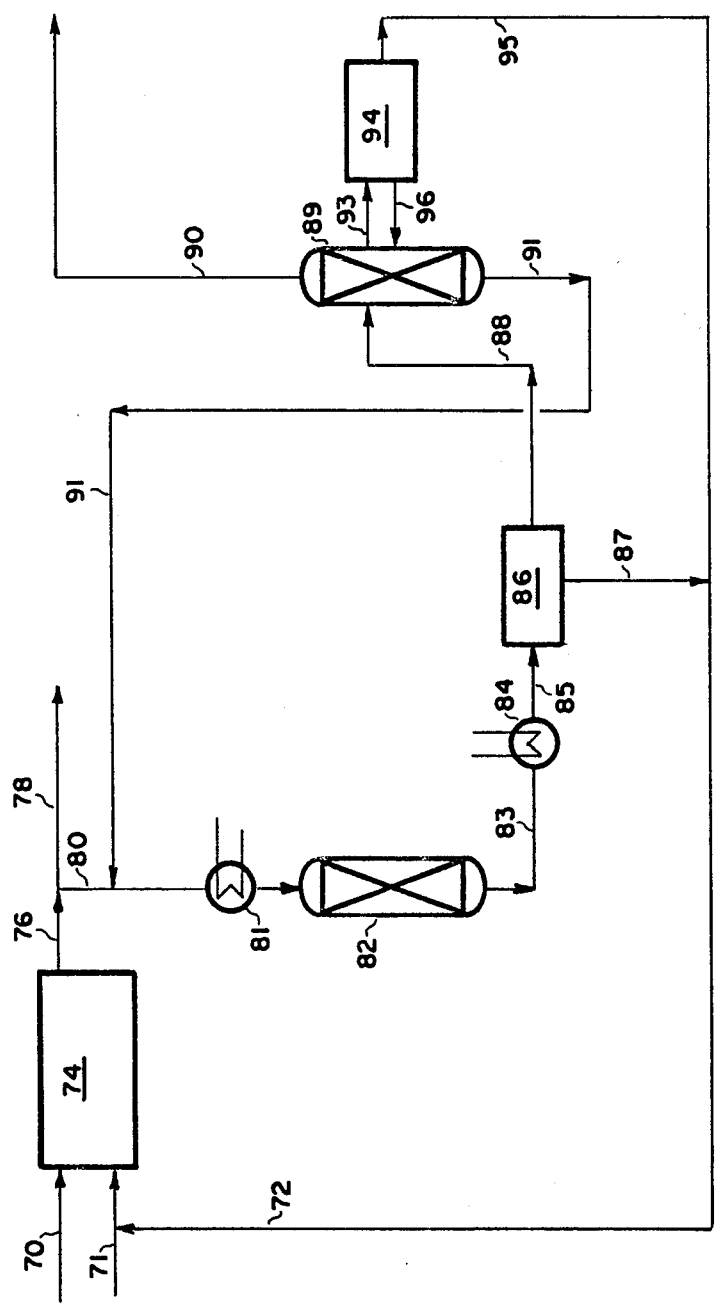
FIG. 4 is a schematic diagram of an ether-decomposition process for high purity isobutene production according to the present invention wherein pervaporation membranes are placed both upstream from, and in conjunction with, the distillation unit.

Another embodiment of the present invention is the use of pervaporation membranes to separate alcohols from ethers and/or hydrocarbons in a process for producing high purity alkenes by the decomposition of ethers. FIG. 4 depicts such a process for producing high purity isobutene by the decomposition of MTBE, although the present invention can be applied to other ether decomposition reactions. An impure $C_4$ feed stream 70 is combined with a methanol feed stream 71 and recycled methanol stream 72 and fed to an MTBE synthesis system 74. The MTBE synthesis system 74 produces a MTBE product stream 76. A portion of the MTBE product stream 76 is collected as final MTBE product stream 78, while another portion of the MTBE product stream 76 is taken off at stream 80 and is heated and vaporized in the heat exchanger 81 and subsequently fed to a decomposition reactor 82 containing a fixed bed of acid cation exchange resin. The decomposition reactor 82 decomposes the MTBE feed to produce an effluent stream 83 containing isobutene/methanol/MTBE, which is cooled and condensed in heat exchanger 84 to produce a liquid mixture 85 which is subsequently fed through a pervaporation membrane system 86. The isobutene/methanol/MTBE mixture is separated by the pervaporation membrane system 86 to produce a high purity methanol permeate vapor 87 and a methanol-depleted liquid concentrate reject stream 88. The high purity methanol permeate vapor stream 87 is withdrawn from the membrane system, cooled and condensed if necessary, and subsequently recycled to the MTBE synthesis reactor 74 as stream 72. The methanol-depleted liquid concentrate reject stream 88 from the pervaporation membrane system 86 is fed to a distillation column 89 to undergo separation. The high purity isobutene stream 90 is taken as overhead product, and a high purity MTBE stream 91 is taken as bottom product and recycled to the feed to the MTBE decomposer 82. A liquid side draw containing isobutene/MTBE/methanol is taken from the distillation column 89 as stream 93 and is fed through a pervaporation membrane 94 where it is separated to form a high purity methanol vapor permeate stream 95 and isobutene/MTBE stream 96. The high purity methanol vapor permeate stream 95 is subsequently combined with the methanol permeate stream from the first pervaporation $$\alpha = \frac{(\text{wt \% alcohol}/100 \text{ wt \%} - \text{wt \% alcohol}) \text{ in permeate}}{(\text{wt \% alcohol}/100 \text{ wt \%} - \text{wt \% alcohol}) \text{ in feed}}$$

TABLE 1

CA MEMBRANE-PERVAPORATION
$CH_3OH/MTBE$

| Experiment # | Temperature (°C.) | Concentration, wt % MeOH Feed + Residue/2 | Permeate | Total Flux (g/hr/$M^2$) | MeOH Flux (g/hr/$M^2$) | Separation Factor α |
|---|---|---|---|---|---|---|
| 0 | 22.5 | 6.89 | 96.72 | 471.6 | 457.4 | 399.7 |
| 1 | 22.5 | 6.90 | 77.63 | 703.2 | 546.9 | 46.9 |
| 2 | 22.5 | 6.63 | 56.40 | 1361.7 | 766.4 | 18.2 |
| 3 | 22.5 | 6.41 | 48.82 | 1410.1 | 688.3 | 13.9 |
| 4 | 22.5 | 6.22 | 93.22 | 561.8 | 524.6 | 207.5 |
| 5 | 22.5 | 3.19 | 93.20 | 256.7 | 238.1 | 416.6 |
| 6 | 22.5 | 1.60 | 88.07 | 119.1 | 104.2 | 454.0 |
| 7 | 22.5 | 0.83 | 50.62 | 93.0 | 48.4 | 122.5 |
| 8 | 36.7 | 2.89 | 68.74 | 565.5 | 386.9 | 74.0 |
| 9 | 48.9 | 2.98 | 62.40 | 881.8 | 550.6 | 54.1 |
| 10 | 25.0 | 3.06 | 88.06 | 256.5 | 225.9 | 233.6 |
| 11* | 22.0 | 5.72 | 93.03 | 784.4 | 729.7 | 219.9 |
| 12* | 22.0 | 2.65 | 98.51 | 340.6 | 335.5 | 2340 |
| 13* | 22.0 | 1.30 | 98.99 | 141.3 | 139.9 | 7471 |
| 14* | 22.0 | 0.76 | 98.18 | 76.8 | 75.4 | 6661 |

*$CH_3OH/MTBE$-HEXANE (50/50 by wt.)

membrane system 86 and recycled as combined methanol stream 72 to the MTBE synthesis step 74. The isobutene/MTBE reject stream 96 from pervaporation membrane system 94 is returned to the distillation column 89 for further separation.

While the above description and flow scheme set out in FIG. 4 disclose one particular embodiment wherein pervaporation membrane systems are incorporated into an MTBE decomposition reaction system, various other embodiments and flow schemes for ether decomposition processes can be designed in accordance with the present invention to employ pervaporation membranes to break alcohol/hydrocarbon and/or alcohol/ether azeotropes. For instance, in the above described flow scheme, two pervaporation membrane systems are specifically recited, one upstream from the distillation column and one in conjunction with the distillation column using a liquid side draw feed. In some instances, only one of these two membrane systems may need to be employed, and such variations in the system will depend upon the specific concentrations and reaction conditions of the rest of the system. Additionally, although not specifically shown, any of the streams depicted in any of the figures of the drawing may include optional compressors, expanders, valves, etc. as needed, depending upon the specific reaction conditions employed and specific purity and pressure of the desired product, without deviating from the spirit of the present invention. As with all of the systems described in the present invention, the above process scheme can employ pervaporation membrane systems containing one or more individual membranes or membrane units, in series or in parallel with internal recycle and similar variations to achieve the most efficient type of separation.

EXAMPLE 1

To illustrate how this invention works, pervaporation experiments were run using cellulose acetate membranes. Results are shown in Table 1 below. The separation factor (α) is defined as:

The α values range from 14 to 400 over a wide range of feed methanol concentration, temperature, and membrane type in the binary system of MTBE/methanol. Even high values of α up to 7471 are observed for a ternary system of MTBE/hexane/methanol. Methanol is more permeable than MTBE and/or hexane because, it is believed, methanol is a smaller molecule, which more easily dissolves in the membrane matrix, causing it to diffuse faster through the membranes. Hence, the difficulty of azeotropic separation by distillation is easily overcome. The presence of $C_6$ or other raffinate components ($C_4$ to $C_7$) actually increases the net methanol flux and improves the selectivity.

EXAMPLE 2

Figure 3:
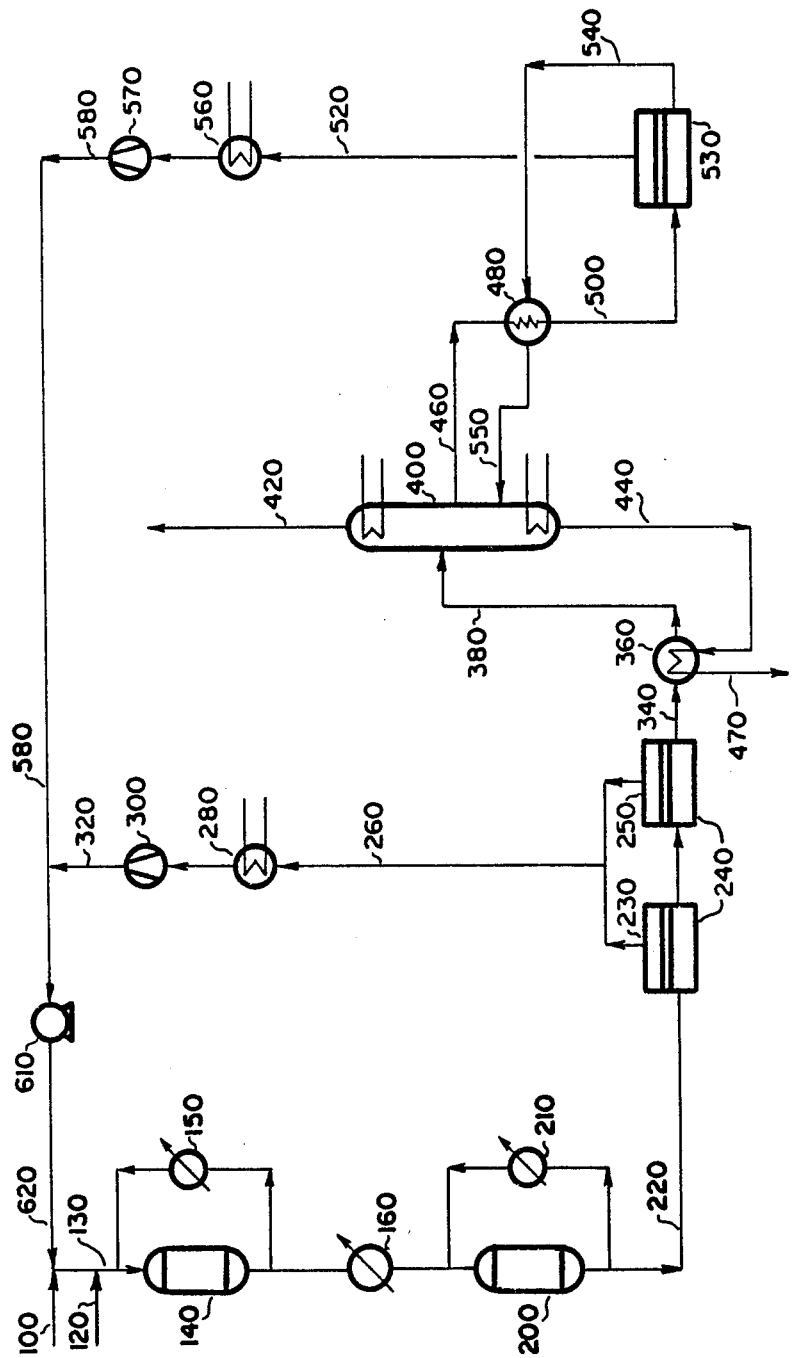
FIG. 3 is a schematic diagram of an etherification process according to the present invention wherein pervaporation membranes are placed both upstream from, and in conjunction with, the distillation unit.

The process of the present invention for an etherification process was carried out via a computer simulation employing a series of pervaporation membranes located upstream from a distillation unit, and also a single pervaporation membrane used in conjunction with the distillation unit with a liquid side draw feed. The process was carried out for the separation of methanol from a methyl t-butyl ether product produced by reacting methanol with isobutylene in a reactor over a suitable catalyst. The process as carried out, is illustrated in FIG. 3. Referring to FIG. 3, feed methanol 100 is mixed with recycled stream 620 and with $C_4$ feed 120 to form a mixed feed 130. The mixed feed 130 is fed to the reactors 140 and 200 with associated heat exchangers 150 and 210, respectively, and also interstage cooler 160. The reactor effluent 220 containing about 5 wt % methanol at 104° F. is fed to a 2-stage pervaporation system 240 comprising membranes 230 and 250 to recover 55% of excess methanol as permeate vapor stream 260. Due to high selectivity of the membrane, the permeate vapor stream 260 contains about 94 wt % methanol. The vapor is cooled and condensed under vacuum in cooler 280 and pump 300 to produce a permeate condensate stream 320. The permeate condensate stream 320 is then mixed with another returning methanol stream 580, to produce a liquid stream 600 which is pumped via pump 610 and recycled to the reactor system as recycle stream 620. The liquid concentrate 340 at 86° F. from the membrane unit is heated to 153° F. in heat exchanger 360 and fed, as stream 380 to the distillation column 400. The feed stream 380 contains about 2.4 wt % methanol. The distillation column 400 operates at 75 psia and contains 27 theoretical stages. A liquid side draw 460 is taken from the distillation column 400 below the feed tray and cooled in heat exchanger 480 to 104° F., to form stream 500 which contains about 5 wt % methanol. Stream 500 is fed to a 1-stage pervaporation system 530 to remove 33% of excess methanol as vapor permeate stream 520 for recycle. The vapor permeate stream 520 is cooled and condensed in condenser 560 under vacuum with vacuum pump 570 to produce a liquid stream 580 containing 98 wt % methanol. Liquid stream 580 is mixed with stream 320 and recycled as stream 620. The liquid concentrate 540 in the pervaporation membrane 530 containing 4% methanol is heated in heat exchanger 480 and returned to column 400 as stream 550 to a tray below the tray from which the side draw stream 460 is taken. C$_4$ raffinate is taken as overhead stream 420 from the distillation column 400, and MTBE product is taken at the bottom as stream 440, and cooled in heat exchanger 360 to produce the final MTBE product stream 470 having a purity of 99.1%. The material balance in process conditions for this process scheme are set out in Table 2 below.

TABLE 2

MASS BALANCE OF FIG. 3

| Stream No. | Flow (lb/hr) | | | |
|---|---|---|---|---|
| | Methanol | C4 | MTBE | Total |
| 100 | 10267 | 0 | 0 | 10267 |
| 120 | 0 | 40228 | 0 | 40228 |
| 220 | 2765 | 22393 | 28109 | 53267 |
| 260, 320 | 1514 | 0 | 91 | 1605 |
| 340, 380 | 1251 | 22393 | 28018 | 51662 |
| 420 | 22 | 22309 | 0 | 22331 |
| 440 | 168 | 84 | 27744 | 27996 |
| 460, 500 | 4507 | 22537 | 63104 | 90148 |
| 520, 580 | 893 | 0 | 274 | 1167 |
| 540, 550 | 3614 | 22537 | 62830 | 88981 |
| 620 | 2407 | 0 | 365 | 2772 |

The above etherification process with pervaporation membrane systems eliminates the conventional methanol purification columns required in prior art processes, thereby reducing the steam consumption by about 10-30% and the capital cost by 5-20%. In addition, the ether product in the recycled methanol stream is reduced significantly compared to conventional prior art methods using the same feed. Due to high selectivity of alcohol by the membrane unit, the improved process allows for even higher methanol/alkene ratios (i.e. >1.5-2.0) to be used in the feed to the synthesis reactor which thereby allows for higher conversions to be attained.

Having thus described the present invention, what is now deemed appropriate for Letters Patent is set out in the following appended claims.

What is claimed is:

1. In a process for the production of ethers whereby an olefin is reacted with an alcohol to produce an alcohol/ether/hydrocarbon raffinate stream in which the alcohol forms azeotrope mixtures with both the ether and raffinate, and said ether is separated from the raffinate by distillation, the improvement for removing alcohols to yield a high purity ether product stream which comprises:

(a) passing said alcohol/ether/hydrocarbon raffinate stream in the liquid state, over a pervaporation membrane capable of breaking the azeotropes and having a high flux and high selectivity for alcohols to produce a vapor alcohol permeate stream and a liquid ether/raffinate reject stream;

(b) recycling the vapor alcohol permeate stream to the reaction step to be reacted with additional olefin feed; and (c) passing the liquid ether/raffinate reject stream to a distillation column to produce a raffinate stream and a high purity ether product stream.

2. The process in accordance with the claim 1 wherein said high purity ether stream is passed over a pervaporation membrane to further separate, as a vapor permeate, alcohol which may be present in said product stream.

3. The process in accordance with claim 1 wherein isobutylene is reacted with methanol to form methyl t-butyl ether.

4. The process in accordance with claim 1 wherein isopentenes are reacted with methanol to form t-amyl methyl ether.

5. The process in accordance with claim 1 wherein over 50% of the alcohol present in the alcohol/ether/raffinate stream is removed by the pervaporation membrane as a gaseous permeate stream.

6. The process in accordance with claim 1 wherein a liquid side draw stream is withdrawn from the distillation column and passed over a pervaporation membrane to remove alcohol as a gaseous permeate and produce a liquid ether/raffinate stream which is returned to the distillation column.

7. The process in accordance with claim 6 wherein the gaseous alcohol permeate produced by passing the side draw stream over the pervaporation membrane is recycled to the reaction step.

8. In a process for the production of ethers whereby an olefin is reacted with an alcohol to produce an alcohol/ether/hydrocarbon raffinate stream in which the alcohol forms azeotrope mixtures with both the ether and raffinate, and said ether is separated from the raffinate by distillation, the improvement for removing alcohols to yield a high purity ether product stream which comprises:

(a) passing said alcohol/ether/hydrocarbon raffinate stream to a distillation column capable of separating ether from raffinate;

(b) withdrawing a liquid side draw stream comprising alcohol, ether and raffinate from the distillation column and passing said stream over a pervaporation membrane to produce a vapor alcohol permeate stream and a liquid ether/raffinate reject stream;

(c) recycling the vapor alcohol permeate stream to the reaction step; and (d) passing the liquid ether/raffinate reject stream back to the distillation column to produce a raffinate stream and a purified ether product stream.

9. The process in accordance with claim 8 wherein isobutylene is reacted with methanol to form methyl t-butyl ether.

10. The process in accordance with claim 8 wherein isopentenes are reacted with methanol to form t-amyl methyl ether.

11. The process in accordance with claim 8 wherein over 50% of the alcohol present in he alcohol/ether/raffinate stream is removed by the pervaporation membrane as a vapor permeate stream.

12. The process in accordance with the claim 8 wherein said high purity ether stream is passed over a pervaporation membrane to further separate, as a vapor permeate, alcohol which may be present in said product stream.

13. The process in accordance with claim 8 wherein the raffinate stream produced in the distillation column is passed over a pervaporation membrane to further separate, as a vapor permeate, alcohol which may be present in said product stream.

14. In a process for the production of high purity alkenes by the decomposition of an ether, wherein said ether is decomposed to form a liquid alcohol/ether/alkene mixture in which the alcohol forms azeotropic mixtures with both the ether and alkene, and said alkenes are separated from the mixture by distillation, the improvement for removing alcohols to yield a high purity alkene product stream which comprises:
(a) passing said liquid alcohol/ether/alkene mixture from the decomposition step over a pervaporation membrane capable of breaking the azeotropes and having a high flux and high selectivity for alcohols to produce a vapor alcohol permeate stream and a liquid ether/alkene reject stream; and
(b) passing the liquid ether/alkene reject stream to a distillation column to produce an ether bottom product and a high purity alkene overhead product.

15. The process in accordance with claim 14 wherein said ether is initially formed by the reaction of an alcohol with an alkene in an ether synthesis reactor.

16. The process in accordance with claim 15 wherein a liquid side draw stream is withdrawn from the distillation column and passed over a pervaporation membrane to remove alcohol as a gaseous permeate to produce a liquid ether/alkene stream which is returned to the distillation column.

17. The process in accordance with claim 15 wherein the vapor alcohol permeate stream is recycled to the ether synthesis reactor.

18. The process in accordance with claim 16 wherein both vapor alcohol permeate streams are recycled to the ether synthesis reactor.

19. The process in accordance with claim 14 wherein the alkene is isobutene or isopentene.

20. In a process for the production of high purity alkenes by the decomposition of an ether, wherein said ether is decomposed to form a liquid alcohol/ether/alkene mixture in which the alcohol forms azeotropic mixtures with both the ether and alkene, and said alkenes are separated from the mixtures by distillation, the improvement for removing alcohols to yield a high purity alkene product stream which comprises:
(a) passing the liquid alcohol/ether/alkene mixture to a distillation column capable of separating ether from alkene;
(b) withdrawing a liquid side draw stream comprising alcohol/ether/alkene from the distillation column and passing said stream over a pervaporation membrane to produce a vapor alcohol permeate stream and a liquid ether/alkene reject stream; and
(c) passing the liquid ether/alkene reject stream back to the distillation column to produce an ether bottom product and a high purity alkene overhead product.

21. The process in accordance with claim 20 wherein said ether is initially formed by the reaction of an alcohol with an alkene in an ether synthesis reactor.

22. The process in accordance with claim 21 wherein the vapor alcohol permeate stream is recycled to the ether synthesis reactor.

23. The process in accordance with claim 20 wherein the alkene is isobutene or isopentene.

* * * * *